United States Patent
Murakami et al.

(10) Patent No.: US 10,472,435 B2
(45) Date of Patent: Nov. 12, 2019

(54) POLYMERIZABLE COMPOSITION AND NOVEL ALKYNE COMPOUND

(71) Applicant: MITSUI CHEMICALS, INC., Minato-ku, Tokyo (JP)

(72) Inventors: Masakazu Murakami, Singapore (SG); Tomoyuki Ando, Omuta (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 170 days.

(21) Appl. No.: 15/548,604

(22) PCT Filed: Feb. 8, 2016

(86) PCT No.: PCT/JP2016/053703
§ 371 (c)(1),
(2) Date: Aug. 3, 2017

(87) PCT Pub. No.: WO2016/126563
PCT Pub. Date: Aug. 18, 2016

(65) Prior Publication Data
US 2018/0066082 A1    Mar. 8, 2018

(30) Foreign Application Priority Data

Feb. 10, 2015    (JP) ................... 2015-024228
Feb. 10, 2015    (JP) ................... 2015-024229

(51) Int. Cl.
| | |
|---|---|
| C08F 38/02 | (2006.01) |
| C08G 75/045 | (2016.01) |
| C07F 9/90 | (2006.01) |
| C07C 321/12 | (2006.01) |
| G02B 1/04 | (2006.01) |
| G02B 7/02 | (2006.01) |
| G02C 7/02 | (2006.01) |

(52) U.S. Cl.
CPC ............ C08F 38/02 (2013.01); C07C 321/12 (2013.01); C07F 9/90 (2013.01); C08G 75/045 (2013.01); G02B 1/04 (2013.01); G02C 7/02 (2013.01)

(58) Field of Classification Search
CPC ......... C08F 38/02; C08G 75/045; G02C 7/02; C07F 9/906; G02B 1/04; C07C 321/12
See application file for complete search history.

(56) References Cited

U.S. PATENT DOCUMENTS

| | | | |
|---|---|---|---|
| 4,066,440 A * | 1/1978 | Rinehart | ............... A01N 47/28 504/327 |
| 4,312,991 A | 1/1982 | Engler et al. | |
| 4,362,662 A | 12/1982 | Engler et al. | |
| 4,363,919 A | 12/1982 | Engler et al. | |
| 4,405,515 A | 9/1983 | Engler et al. | |
| 6,204,311 B1 | 3/2001 | Morijiri et al. | |
| 6,300,464 B2 | 10/2001 | Morijiri et al. | |
| 6,458,917 B2 | 10/2002 | Morijiri et al. | |
| 7,534,899 B2 | 5/2009 | Jeong et al. | |
| 7,723,318 B2 | 5/2010 | Otsuji et al. | |
| 7,906,494 B2 | 3/2011 | Otsuji et al. | |
| 7,998,944 B2 | 8/2011 | Otsuji et al. | |
| 8,097,694 B2 | 1/2012 | Jeong et al. | |
| 8,293,864 B2 | 10/2012 | Murakami et al. | |
| 8,426,551 B2 | 4/2013 | Murakami et al. | |
| 8,859,698 B2 | 10/2014 | Tang et al. | |
| 2001/0002413 A1 | 5/2001 | Morijiri et al. | |
| 2002/0019511 A1 | 2/2002 | Morijiri et al. | |
| 2007/0120120 A1 | 5/2007 | Jeong et al. | |
| 2007/0191615 A1 | 8/2007 | Otsuji et al. | |
| 2007/0270548 A1* | 11/2007 | Bojkova | ............ C08G 18/3234 525/123 |
| 2009/0263932 A1 | 10/2009 | Jeong et al. | |
| 2010/0179333 A1 | 7/2010 | Otsuji et al. | |
| 2010/0190949 A1 | 7/2010 | Otsuji et al. | |
| 2010/0240862 A1 | 9/2010 | Murakami et al. | |
| 2012/0148958 A1 | 6/2012 | Tang et al. | |

(Continued)

FOREIGN PATENT DOCUMENTS

| | | |
|---|---|---|
| EP | 2123695 A1 | 11/2009 |
| JP | 55-151580 A | 11/1980 |

(Continued)

OTHER PUBLICATIONS

CAS Registry No. 70446-04-7 (Nov. 16, 1984).
CAS Registry No. 1220112-11-7 (Apr. 23, 2010).
Notification of Reason for Refusal issued by the Korean Intellectual Property Office in corresponding Korean Patent Application No. 10-2017-7021463 dated Jun. 14, 2018 (14 pages including partial English translation).
International Search Report (PCT/ISA/210) dated Apr. 12, 2016, by the Japanese Patent Office as the International Searching Authority for International Application No. PCT/JP2016/053703.
Written Opinion (PCT/ISA/237) dated Apr. 12, 2016, by the Japanese Patent Office as the International Searching Authority for International Application No. PCT/JP2016/053703.

(Continued)

Primary Examiner — Shane Fang
(74) Attorney, Agent, or Firm — Buchanan, Ingersoll & Rooney PC

(57) ABSTRACT

Provided is a polymerizable composition including an alkyne compound represented by the following general formula (1):

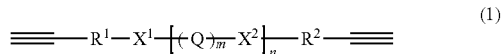

wherein, in general formula (1), $X^1$ and $X^2$ represent a sulfur atom, an oxygen atom, or an NH group and may be the same or different from each other, Q represents an alkylene group having 1 or 2 carbon atoms, a carbonyl group, or a thiophenylene group in which one of carbon atoms is substituted by an antimony atom, $R^1$ and $R^2$ represent an alkylene group having 1 or 2 carbon atoms and may be the same or different from each other, and m and n each represent 0 or 1.

7 Claims, No Drawings

(56) References Cited

U.S. PATENT DOCUMENTS

| | | | |
|---|---|---|---|
| 2013/0018169 A1 | 1/2013 | Murakami et al. | |
| 2016/0280840 A1* | 9/2016 | Murakami | C08G 18/8133 |

FOREIGN PATENT DOCUMENTS

| | | |
|---|---|---|
| JP | 63-301227 A | 12/1988 |
| JP | 09-040615 A | 2/1997 |
| JP | 11-322930 A | 11/1999 |
| JP | 2001-019724 A | 1/2001 |
| JP | 2007-176929 A | 7/2007 |
| JP | 2009-275023 A | 11/2009 |
| JP | 2013-502463 A | 1/2013 |
| JP | 2013-239426 A | 11/2013 |
| WO | WO 2005/095490 A1 | 10/2005 |
| WO | WO 2008/102545 A1 | 8/2008 |
| WO | WO 2014/157664 A1 | 10/2014 |

OTHER PUBLICATIONS

Nakahashi et al., "Synthesis of Sulfur-Containing Hyperbranched Polymers by the Bisthiolation Polymerization of Diethynyl Disulfide Derivatives", Journal of Polymer Science: Part A: Polymer Chemistry, 2007, 45, pp. 3580-3587.

Braverman et al., "Synthesis and reactivity of dipropargylic disulfides: tandem rearrangements, cyclization, and oxidative dimerization", Tetrahedron, 2010, 66, pp. 1925-1930.

Yamamoto et al., "Cp*RuCl-Catalyzed [2 + 2 + 2] Cycloadditions of $\alpha,\omega$-Diynes with Electron-Deficient Carbon-Heteroatom Multiple Bonds Leading to Heterocycles", Journal of the American Chemical Society, 2005, 127, pp. 605-613.

"19619 Organic hardeners for photographic material", Research Disclosure, Aug. 1980, pp. 342-343.

Inoue et al., "Cobaltocene-CatalyzedReaction of Carbon Dioxide with Propargyl Alcohols", Bull. Chem. Soc. Jpn., 1987, 60, pp. 1204-1206.

Yeong-Soon Gal et al.: "Cyclopolymerization of Dipropargyl Sulfide by Transition Metal Catalysts," Journal of Polymer Science, Polymer Letters Edition, vol. 26, No. 2, Feb. 1, 1988, pp. 115-121.

In-Sook Lee et al.: "Synthesis of conjugated spirocyclic polymers: Cyclopolymerization of 1,1-dipropargyl-1-silacycloalkanes by transition metal catalysts," Journal of Industrial and Engineering Chemistry, The Korean Society of Industrial and Engineering Chemistry, Korea, vol. 14, No. 6, Nov. 1, 2008, pp. 720-725.

Extended Search Report issued by the European Patent Office in corresponding European Patent Application No. 16749207.3-1107 dated Sep. 11, 2018 (7 pages).

Kokelenberg et al.: "Organic hardeners for photographic material," Research Disclosure database No. 196019, Certified Document,The Industry Standard Disclosure Publication Service, Dec. 31, 1980 (7 pages).

Office Action issued by the Chinese Patent Office in corresponding Chinese Patent Application No. 201680008489.4 dated Dec. 5, 2018 (22 pages).

Kuhling et al.: "Poly(2,4-hexadiyn-1,6-ylene carbonate). Synthesis and Topochemical Cross-Linking Reaction," Macromolecules, American Chemical Society, US, vol. 23, No. 19, Sep. 17, 1990, pp. 4192-4195.

Communication pursuant to Rules 70(2) and 70a(2) EPC issued by the European Patent Office in corresponding European Patent Application No. 16749207.3-1107 dated Nov. 23, 2018 (8 pages).

* cited by examiner

POLYMERIZABLE COMPOSITION AND NOVEL ALKYNE COMPOUND

TECHNICAL FIELD

The present invention relates to a polymerizable composition and a novel alkyne compound.

BACKGROUND ART

In recent years, a transparent organic polymer material has been used as a transparent material to replace inorganic glass. In the case where such a material is used in, for example, optical applications such as spectacle lenses, it is required to have a high refractive index while having generally required properties such as transparency, thermal properties, and mechanical properties.

As a related art relating to such a resin, Patent Document 1 describes examples of using a compound having a disulfide bond. Further, Non-Patent Document 1 describes that a resin is obtained by copolymerizing a compound having sulfur atom and a triple bond with a polythiol, although optical properties of such a resin are not known.

Further, as a related art relating to a resin, there is a disclosure of Patent Document 2. The same document describes a metal-containing thietane compound. Further, a high refractive index optical material having a refractive index (nd) of more than 1.7 is described therein. Further, there is a description in Patent Document 3 that a high refractive index optical material having a refractive index (ne) of more than 1.8 is obtained by using an antimony thietane compound. Further, Patent Document 4 describes that an optical material having a refractive index of 1.643 is obtained by using an antimony arylthiolate compound. Patent Document 5 describes that an optical material having a refractive index of 1.730 is obtained from a polymerizable composition containing a propargyl isocyanate and a polythiol compound.

In addition, Patent Document 6, and Non-Patent Documents 2 to 5 disclose compounds having triple bonds at both terminals thereof.

RELATED DOCUMENTS

Patent Documents

[Patent Document 1] JPH11-322930
[Patent Document 2] WO 2005-095490
[Patent Document 3] WO 2008-102545
[Patent Document 4] JP2009-275023
[Patent Document 5] WO 2014-157664
[Patent Document 6] JPH9-40615

Non-Patent Documents

[Non-Patent Document 1] Journal of Polymer Science: Part A, Polymer Chemistry, 2007, pp 3580 to 3587
[Non-Patent Document 2] Tetrahedron Volume 66, Issue 10, pp 1925 to 1930, 2010
[Non-Patent Document 3] Journal of the American Chemical Society Volume 127, Issue 2, pp 605 to 613, 2005
[Non-Patent Document 4] RESEARCH DISCLOSURE August 1980, 19619 Organic hardeners for photographic material, pp 342 to 343
[Non-Patent Document 5] Bull. Chem. Soc. Jpn., pp 1204 to 1206, Vol. 60, No. 3, 1987

SUMMARY OF THE INVENTION

An object of the present invention is to obtain a polymerizable composition including a predetermined compound with which an optical material having a high refractive index can be obtained, and a novel alkyne compound.

That is, the present invention is as follows.

[1] A polymerizable composition including an alkyne compound represented by the following general formula (1):

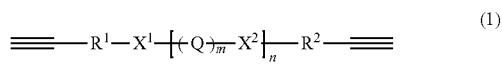

wherein, in general formula (1), $X^1$ and $X^2$ represent a sulfur atom, an oxygen atom, or an NH group and may be the same or different from each other, Q represents an alkylene group having 1 or 2 carbon atoms, a carbonyl group, or a thiophenylene group in which one of carbon atoms is substituted by an antimony atom, $R^1$ and $R^2$ represent an alkylene group having 1 or 2 carbon atoms and may be the same or different from each other, and m and n each represent 0 or 1.

[2] The polymerizable composition according to [1], including an alkyne compound represented by the following general formula (2) or (3):

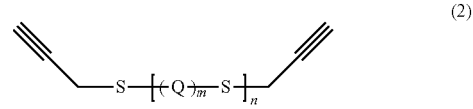

wherein, in general formula (2), Q represents an alkylene group having 1 or 2 carbon atoms, or a thiophenylene group in which one of carbon atoms is substituted by an antimony atom, and m and n each represent 0 or 1,

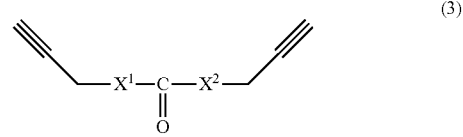

wherein, in general formula (3), $X^1$ and $X^2$ represent a sulfur atom, an oxygen atom, or an NH group and may be the same or different from each other.

[3] The polymerizable composition according to [1] or [2], in which the thiophenylene group in which one of carbon atoms is substituted by an antimony atom is a divalent group represented by the following Formula (4):

wherein, in general formula (4), * represents a bonding hand.

[4] The polymerizable composition according to any one of [1] to [3], further including a thiol compound.

[5] The polymerizable composition according to [4], in which the thiol compound includes at least one kind of polythiol compounds selected from 4-mercaptomethyl-1,8-dimercapto-3,6-dithiaoctane, 4,8 or 4,7 or 5,7-dimercaptomethyl-1,11-dimercapto-3,6,9-trithiaundecane, pentaerythritol tetrakis(2-mercaptoacetate), pentaerythritol tetrakis(3-mercaptopropionate), 2,5-bis(mercaptomethyl)-1,4-dithiane, bis(mercaptoethyl)sulfide, 1,1,3,3-tetrakis(mercaptomethylthio)propane, 4,6-bis(mercaptomethylthio)-1,3-dithiane, and 2-(2,2-bis(mercaptomethylthio)ethyl)-1,3-dithietane.

[6] A molded product obtained by curing the polymerizable composition according to any one of [1] to [5].

[7] An optical material comprised of the molded product according to [6].

[8] A plastic lens comprised of the molded product according to [6].

[9] An alkyne compound represented by the following general formula (5):

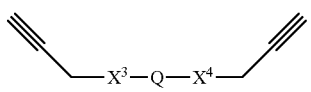

(5)

wherein, in general formula (5), $X^3$ and $X^4$ represent a sulfur atom or an NH group and may be the same or different from each other, and Q represents an alkylene group having 1 or 2 carbon atoms, a carbonyl group, or a thiophenylene group in which one of carbon atoms is substituted by an antimony atom.

[10] The alkyne compound according to [9], in which the thiophenylene group in which one of carbon atoms is substituted by an antimony atom is a group represented by the following Formula (4):

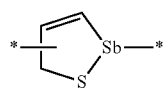

(4)

wherein, in general formula (4), * represents a bonding hand.

According to the present invention, it is possible to provide a polymerizable composition including a predetermined compound with which a transparent optical material having a high refractive index is obtained, and a novel alkyne compound.

DESCRIPTION OF EMBODIMENTS

Hereinafter, the present invention will be described.
[Polymerizable Composition]
The polymerizable composition according to the present invention includes an alkyne compound represented by the following general formula (1).

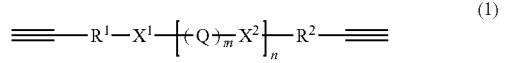

(1)

In general formula (1), $X^1$ and $X^2$ represent a sulfur atom, an oxygen atom, or an NH group, and may be the same or different from each other. $X^1$ and $X^2$ may be a combination of sulfur atoms, a combination of a sulfur atom and an NH group, or a combination of oxygen atoms.

Q represents an alkylene group having 1 or 2 carbon atoms, a carbonyl group, or a thiophenylene group in which one of carbon atoms is substituted by an antimony atom.

With respect to the "thiophenylene group in which one of carbon atoms is substituted by an antimony atom", the position of an antimony atom is not particularly limited. From the viewpoint of the effect of the present invention, it is possible to use a group represented by the following general formula (4).

(4)

In general formula (4), * represents a bonding hand.

In general formula (1), $R^1$ and $R^2$ represent an alkylene group having 1 or 2 carbon atoms, and may be the same or different from each other. $R^1$ and $R^2$ are preferably an alkylene group having one carbon atom.

m and n each represent 0 or 1.

According to the polymerizable composition including such an alkyne compound, a transparent optical material having a high refractive index can be obtained.

From the viewpoint of the effect of the present invention, the alkyne compound is preferably a compound represented by the following general formula (2) or (3).

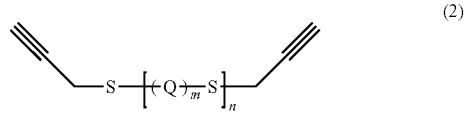

(2)

In general formula (2), Q represents an alkylene group having 1 or 2 carbon atoms, or a thiophenylene group in which one of carbon atoms is substituted by an antimony atom. m and n have the same definition as in general formula (1).

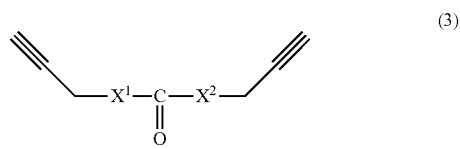

(3)

In general formula (3), $X^1$ and $X^2$ have the same definition as in general formula (1).

Among the alkyne compounds as described above, a novel compound may be, for example, the following compound.

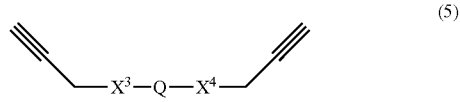

(5)

In general formula (5), $X^3$ and $X^4$ represent a sulfur atom or an NH group, and are preferably a combination of sulfur atom, or a combination of a sulfur atom and an NH group. Q has the same definition as in general formula (1) and is preferably an alkylene group having one carbon atom, a carbonyl group, or a thiophenylene group in which one of carbon atoms is substituted by an antimony atom.

The compounds represented by the following general formulae (1-1) to (1-5) may be preferably used as the alkyne compound represented by general formula (1).

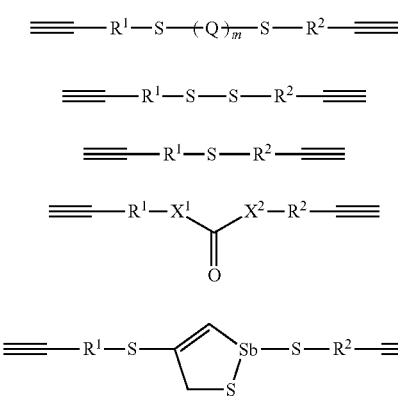

In general formulae (1-1) to (1-5), $R^1$, $R^2$, Q, $X^1$, and $X^2$ have the same definition as in general formula (1). In this case, m is 1.

These compounds can be obtained as follows.

(Compound of General Formula (1-1))

The compound represented by general formula (1-1) can be produced as follows.

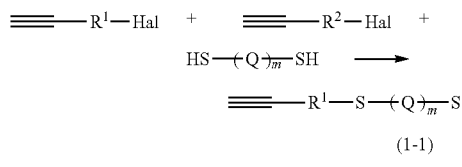

The compound represented by general formula (1-1) is obtained by charging dropwise an alkyl halide compound having an alkyne group at the terminal thereof into a solution which is obtained by mixing and stirring a dithiol compound and a basic compound.

In order to achieve an efficient reaction when carrying out the reaction, it is preferred to use a basic compound as a scavenger of the resulting hydrogen halide.

Examples of such a basic compound include inorganic bases such as sodium hydroxide, potassium hydroxide, lithium hydroxide, sodium carbonate, potassium carbonate, lithium carbonate, sodium bicarbonate, potassium bicarbonate, lithium bicarbonate, magnesium hydroxide, and calcium hydroxide; and organic bases such as pyridine, triethylamine, dimethylaniline, diethylaniline, and 1,8-diazabicyclo[5.4.0]-7-undecene.

(Compound of General Formula (1-2))

The compound represented by general formula (1-2) can be produced as follows.

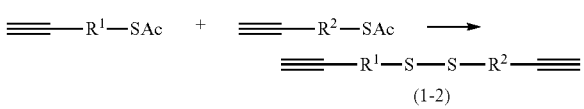

The compound represented by general formula (1-2) is produced by charging dropwise an iodine solution into a solution which is obtained by mixing and stirring a thioacetic acid ester compound having an alkyne group at the terminal thereof and caustic water.

Since the disulfide compound having an alkyne group at the terminal thereof synthesized by the above-mentioned method has a high self-reactivity, it is desired to ensure reaction and handling at low temperatures. Specifically, the operation from reaction to removal can be performed at a temperature of −20° C. to 10° C.

(Compound of General Formula (1-3))

The compound represented by general formula (1-3) can be obtained as follows.

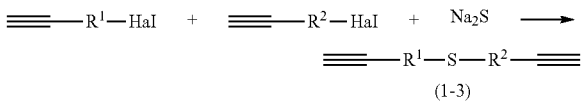

The compound represented by general formula (1-3) is produced by charging dropwise an alkyl halide compound having an alkyne group at the terminal thereof into a solution which is obtained by mixing and stirring sodium sulfide and dimethylformamide.

The reaction temperature of the compounds shown above is not particularly limited and is usually in the range of −78° C. to 200° C., and preferably −78° C. to 100° C.

(Compound of General Formula (1-4))

The compound represented by general formula (1-4) can be obtained as follows.

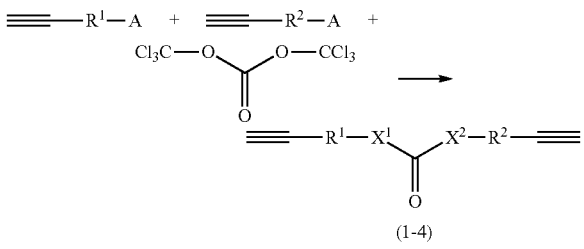

In the above reaction formula, "A" represent a hydroxyl group, a thiol group, or an isocyanate group, and may be the same or different from each other.

The compound represented by general formula (1-4) is obtained by charging dropwise a mixed solution of an alcohol or thiol compound having an alkyne group at the terminal thereof and a base to a solution of triphosgene or phosgene. Alternatively, the compound represented by general formula (1-4) is obtained by charging dropwise an alcohol or thiol compound having an alkyne group at the terminal thereof to a solution of an isocyanate compound having an alkyne group at the terminal thereof.

The solvent that can be used in the above reaction is not particularly limited as long as it is a reaction-inert solvent, and examples thereof include hydrocarbon-based solvents such as petroleum ether, hexane, benzene, toluene, xylene, and mesitylene;

ether-based solvents such as diethyl ether, tetrahydrofuran, and diethylene glycol dimethyl ether;

ketone-based solvents such as acetone, methyl ethyl ketone, and methyl isobutyl ketone;

ester-based solvents such as ethyl acetate, butyl acetate, and amyl acetate; and chlorinated solvents such as methylene chloride, chloroform, chlorobenzene, and dichlorobenzene.

Examples of the base include inorganic bases such as sodium hydroxide, potassium hydroxide, lithium hydroxide, sodium carbonate, potassium carbonate, lithium carbonate, sodium bicarbonate, potassium bicarbonate, lithium bicarbonate, magnesium hydroxide, and calcium hydroxide;

alkali metal alkoxides such as sodium methoxide, sodium ethoxide, and potassium t-butoxide; and organic bases such as pyridine, triethylamine, dimethylaniline, diethylaniline, and 1,8-diazabicyclo[5.4.0]-7-undecene.

The reaction temperature is not particularly limited and is usually in the range of −78° C. to 200° C., and preferably −78° C. to 100° C.

The reaction time is affected by the reaction temperature, but it is usually from several minutes to 100 hours.

(Compound of General Formula (1-5))

The compound represented by general formula (1-5) can be obtained, for example, by reacting a thioacetylation product of propyne or 1-butyne, propargyl thiol or 3-butyne-1-thiol with an antimony halide in the presence of a reaction-inert solvent and a base.

The solvent that can be used in the above reaction is not particularly limited as long as it is a reaction-inert solvent, and examples thereof include hydrocarbon-based solvents such as petroleum ether, hexane, benzene, toluene, xylene, and mesitylene;

ether-based solvents such as diethyl ether, tetrahydrofuran, and diethylene glycol dimethyl ether;

ketone-based solvents such as acetone, methyl ethyl ketone, and methyl isobutyl ketone;

ester-based solvents such as ethyl acetate, butyl acetate, and amyl acetate;

chlorinated solvents such as methylene chloride, chloroform, chlorobenzene, and dichlorobenzene;

aprotic polar solvents such as N,N-dimethyl formamide, N,N-dimethyl acetamide, N,N-dimethyl imidazolidinone, and dimethyl sulfoxide;

sulfur-containing solvents such as tetrahydrothiophene, thiophene, sulfolane, trimethylene sulfide, diethyl sulfide, di-n-propyl sulfide, di-t-butyl sulfide, 3-mercaptothietane, and bis(2-mercaptoethyl)sulfide;

aliphatic alcohols such as methanol, ethanol, propanol, isopropanol, butanol, and t-butanol; and water.

Examples of the base include inorganic bases such as sodium hydroxide, potassium hydroxide, lithium hydroxide, sodium carbonate, potassium carbonate, lithium carbonate, sodium bicarbonate, potassium bicarbonate, lithium bicarbonate, magnesium hydroxide, and calcium hydroxide;

alkali metal alkoxides such as sodium methoxide, sodium ethoxide, and potassium t-butoxide; and organic bases such as pyridine, triethylamine, dimethylaniline, diethylaniline, and 1,8-diazabicyclo[5.4.0]-7-undecene.

Examples of the antimony halide that can be used in the present invention include antimony chloride and antimony bromide. From the viewpoint of easy availability, preferred is antimony chloride.

The reaction temperature is not particularly limited and is usually in the range of −78° C. to 200° C., and preferably −78° C. to 100° C.

The reaction time is affected by the reaction temperature, but it is usually from several minutes to 100 hours.

In the above reaction, the amount of the thioacetylation product of propyne or 1-butyne, propargyl thiol or 3-butyne-1-thiol to be used is not particularly limited. The amount of the thioacetylation product, propargyl thiol or 3-butyne-1-thiol to be used is usually equal to or more than 0.01 mol and equal to or less than 20 mol with respect to 1 mol of halogen atoms contained in the antimony halide. The amount of the thioacetylation product, propargyl thiol or 3-butyne-1-thiol to be used is preferably equal to or more than 0.1 mol and equal to or less than 5 mol, and more preferably equal to or more than 0.5 mol and equal to or less than 1.5 mol.

Compounds represented by the following Formulae (1a) to (1h) can be preferably used as the alkyne compound represented by general formula (1).

$$\equiv\!-\!CH_2\!-\!S\!-\!S\!-\!CH_2\!-\!\equiv \quad (1a)$$

$$\equiv\!-\!CH_2\!-\!S\!-\!CH_2CH_2\!-\!S\!-\!CH_2\!-\!\equiv \quad (1b)$$

$$\equiv\!-\!CH_2\!-\!S\!-\!CH_2\!-\!\equiv \quad (1c)$$

(1d)

$$\equiv\!-\!CH_2\!-\!O\!-\!\underset{\underset{O}{\parallel}}{C}\!-\!O\!-\!CH_2\!-\!\equiv$$

$$\equiv\!-\!CH_2\!-\!S\!-\!CH_2\!-\!S\!-\!CH_2\!-\!\equiv \quad (1e)$$

(1f)

$$\equiv\!-\!CH_2\!-\!S\!-\!\underset{\underset{O}{\parallel}}{C}\!-\!S\!-\!CH_2\!-\!\equiv$$

(1g)

$$\equiv\!-\!CH_2\!-\!S\!-\!\underset{\underset{O}{\parallel}}{C}\!-\!\overset{H}{N}\!-\!CH_2\!-\!\equiv$$

(1h)

$$\equiv\!-\!CH_2\!-\!S\!-\!\underset{S}{\overset{\diagup\!\diagdown}{Sb}}\!-\!S\!-\!CH_2\!-\!\equiv$$

Hereinafter, reaction schemes for compounds of Formula (1a), Formula (1e), Formula (1f), Formula (1g), and Formula (1h) are shown as specific examples.

$$\equiv\!\!-\!\!SAc \xrightarrow[H_2O]{NaOHaq} \xrightarrow{I_2} \equiv\!-\!CH_2\!-\!S\!-\!S\!-\!CH_2\!-\!\equiv$$

(1a)

In the above scheme, NaOHaq represents a sodium hydroxide aqueous solution, and Ac represents an acetyl group.

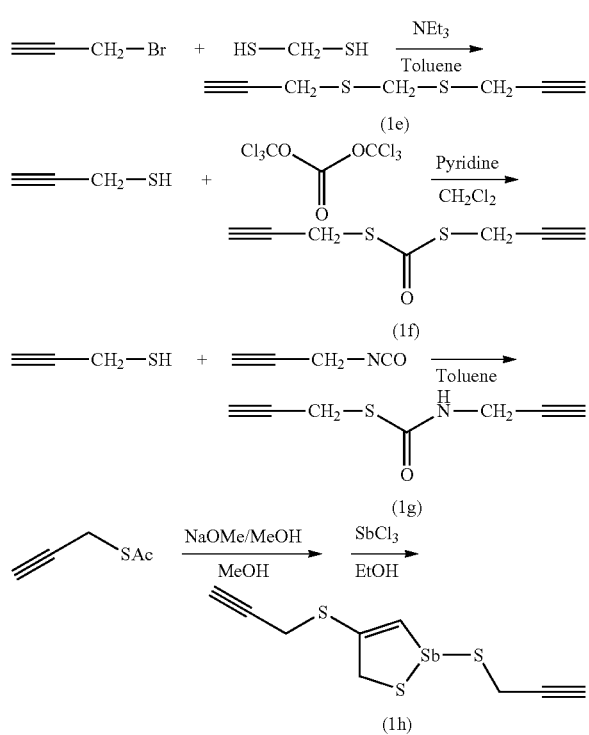

In the above schemes, Ac represents an acetyl group, Me represents a methyl group, and Et represents an ethyl group.

The polymerizable composition of the present invention includes an alkyne compound represented by general formula (1).

Further, a thiol compound can be contained in conjunction with this alkyne compound, and the polymerizable composition of the present invention can be suitably used as a polymerizable composition for an optical material.

The thiol compound used in the polymerizable composition is a compound containing at least one kind of thiol groups (SH groups) in the molecule. As the thiol compound, for example, a compound having any structure may also be used as long as it is compatible with the compound represented by general formula (1).

In the thiol compound, examples of a monovalent thiol compound include aliphatic mercaptan compounds such as methyl mercaptan, ethyl mercaptan, propyl mercaptan, butyl mercaptan, octylmercaptan, dodecyl mercaptan, tert-dodecyl mercaptan, hexadecyl mercaptan, octadecylmercaptan, cyclohexylmercaptan, benzyl mercaptan, ethyl phenyl mercaptan, 2-mercaptomethyl-1,3-dithiolane, 2-mercaptomethyl-1,4-dithiane, 1-mercapto-2,3-epithiopropane, 1-mercaptomethylthio-2,3-epithiopropane, 1-mercaptoethylthio-2,3-epithiopropane, 3-mercaptothietane, 2-mercaptothietane, 3-mercaptomethylthiothietane, 2-mercaptomethylthiothietane, 3-mercaptoethylthiothietane, and 2-mercaptoethylthiothietane; aromatic mercaptan compounds such as thiophenol and mercaptotoluene; and compounds containing a hydroxy group in addition to a mercapto group, such as 2-mercaptoethanol and 3-mercapto-1,2-propanediol.

Examples of the polyvalent thiol (polythiol) compound include aliphatic polythiol compounds such as 1,1-methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, 1,1-bis(mercaptomethyl)cyclohexane, thiomalic acid bis(2-mercaptoethyl ester), 2,3-dimercapto-1-propanol (2-mercaptoacetate), 2,3-dimercapto-1-propanol(3-mercaptopropionate), diethylene glycol bis(2-mercaptoacetate), diethylene glycol bis(3-mercaptopropionate), 1,2-dimercaptopropyl methyl ether, 2,3-dimercaptopropyl methyl ether, 2,2-bis(mercaptomethyl)-1,3-propanedithiol, bis(2-mercaptoethyl)ether, ethylene glycol bis(2-mercaptoacetate), ethylene glycol bis(3-mercaptopropionate), trimethylolpropane bis(2-mercaptoacetate), trimethylolpropane bis(3-mercaptopropionate), pentaerythritol tetrakis(2-mercaptoacetate), pentaerythritol tetrakis(3-mercaptopropionate), tetrakis(mercaptomethyl)methane, and 1,1,1,1-tetrakis(mercaptomethyl)methane;

aromatic polythiol compounds such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,2,4-tris(mercaptoethyl)benzene, 1,3,5-tris(mercaptoethyl)benzene, 2,5-toluenedithiol, 3,4-toluenedithiol, 1,3-di(p-methoxyphenyl)propane-2,2-dithiol, 1,3-diphenylpropane-2,2-dithiol, phenylmethane-1,1-dithiol, and 2,4-di(p-mercaptophenyl)pentane;

aromatic polythiol compounds each containing a sulfur atom in addition to a mercapto group, such as 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene, and 1,3,5-tris(mercaptoethylthio)benzene, and nuclear alkylated products thereof;

aliphatic polythiol compounds each containing a sulfur atom in addition to a mercapto group, such as bis(mercaptomethyl)sulfide, bis(mercaptomethyl)disulfide, bis(mercaptoethyl)sulfide, bis(mercaptoethyl)disulfide, bis(mercaptopropyl)sulfide, bis(mercaptomethylthio)methane, bis(2-mercaptoethylthio)methane, bis(3-mercaptopropylthio)methane, 1,2-bis(mercaptomethylthio)ethane, 1,2-bis(2-mercaptoethylthio)ethane, 1,2-bis(3-mercaptopropyl)ethane, 1,3-bis(mercaptomethylthio)propane, 1,3-bis(2-mercaptoethylthio)propane, 1,3-bis(3-mercaptopropylthio)propane, 1,2,3-tris(mercaptomethylthio)propane, 1,2,3-tris(2-mercaptoethylthio)propane, 1,2,3-tris(3-mercaptopropylthio)propane, 1,2-bis[(2-mercaptoethyl)thio]-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, bis(1,3-dimercaptopropyl)sulfide, 2,5-dimercapto-1,4-dithiane, 2,5-bis(mercaptomethyl)-1,4-dithiane, 2,5-dimercaptomethyl-2,5-dimethyl-1,4-dithiane, bis(mercaptomethyl)disulfide, bis(mercaptoethyl)disulfide, bis(mercaptopropyl)disulfide, and 4-mercaptomethyl-1,8-dimercapto-3,6-dithiaoctane, and esters of thioglycolic acid and mercaptopropionic acid thereof;

aliphatic polythiol compounds each containing a sulfur atom and an ester bond in addition to a mercapto group, such as hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxypropyl sulfide bis(2-mercaptoacetate), hydroxypropyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), hydroxypropyl disulfide bis(2-mercaptoacetate), hydroxypropyl disulfide bis(3-mercaptopropionate), 2-mercaptoethyl ether bis(2-mercaptoacetate), 2-mercaptoethyl ether bis(3-mercaptopropionate), 1,4-dithiane-2,5-diol bis(2-mercaptoacetate), 1,4-dithiane-2,5-diol bis(3-mercaptopropionate), thiodiglycolic acid bis(2-mercaptoethyl ester), thiodipropionic acid bis(2-mercaptoethyl ester), 4,4-thiodibutyric acid bis(2-mercaptoethyl ester), dithiodiglycolic acid bis(2-mercaptoethyl ester), dithiodipropionic acid bis(2-mercaptoethyl ester), 4,4-dithiodibutyric acid bis(2-mercaptoethyl ester), thiodiglycolic acid bis(2,3-dimercaptopropyl ester), thiodipropionic acid bis(2,3-dimercaptopropyl ester), dithioglycolic acid bis(2,3-dimercaptopropyl ester), and dithiodipropionic acid bis(2,3-dimercaptopropyl ester);

heterocyclic compounds each containing a sulfur atom in addition to a mercapto group, such as 3,4-thiophenedithiol and 2,5-dimercapto-1,3,4-thiadiazole;

compounds each containing a hydroxy group in addition to a mercapto group, such as glycerin di(mercaptoacetate), 1-hydroxy-4-mercaptocyclohexane, 2,4-dimercaptophenol, 2-mercaptohydroquinone, 4-mercaptophenol, 3,4-dimercapto-2-propanol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), pentaerythritol bis(3-mercaptopropionate), pentaerythritol tris(thioglycolate), dipentaerythritol pentakis(3-mercaptopropionate), hydroxymethyl-tris(mercaptoethylthiomethyl)methane, and 1-hydroxyethylthio-3-mercaptoethylthiobenzene;

compounds each having a dithioacetal or dithioketal skeleton, such as 1,1,3,3-tetrakis(mercaptomethylthio)propane, 4,6-bis(mercaptomethylthio)-1,3-dithiane, 2-(2,2-bis(mercaptomethylthio)ethyl)-1,3-dithietane, 1,1,2,2-tetrakis(mercaptomethylthio)ethane, 1,1,5,5-tetrakis(mercaptomethylthio)-3-thiapentane, 1,1,6,6-tetrakis(mercaptomethylthio)-3,4-dithiahexane, 2,2-bis(mercaptomethylthio)ethanethiol, 2-(4,5-dimercapto-2-thiapentyl)-1,3-dithiacyclopentane, 2,2-bis(mercaptomethyl)-1,3-dithiacyclopentane, 2,5-bis(4,4-bis(mercaptomethylthio)-2-thiabutyl)-1,4-dithiane, 2,2-bis(mercaptomethylthio)-1,3-propanedithiol, 3-mercaptomethylthio-1,7-dimercapto-2,6-dithiaheptane, 3,6-bis(mercaptomethylthio)-1,9-dimercapto-2,5,8-trithianonane, 4,6-bis(mercaptomethylthio)-1,9-dimercapto-2,5,8-trithianonane, 3-mercaptomethylthio-1,6-dimercapto-2,5-dithiahexane, 1,1,9,9-tetrakis(mercaptomethylthio)-5-(3,3-bis(mercaptomethyl thio)-1-thiapropyl)3,7-dithianonane, tris(2,2-bis(mercaptomethylthio)ethyl)methane, tris(4,4-bis(mercaptomethylthio)-2-thiabutyl)methane, tetrakis(2,2-bis(mercaptomethylthio)ethyl)methane, tetrakis(4,4-bis(mercaptomethylthio)-2-thiabutyl)methane, 3,5,9,11-tetrakis(mercaptomethylthio)-1,13-dimercapto-2,6,8,12-tetrathiatridecane, 3,5,9,11,15,17-hexakis(mercaptomethylthio)-1,19-dimercapto-2,6,8,12,14,18-hexathianonadecane, 9-(2,2-bis(mercaptomethylthio)ethyl)-3,5,13,15-tetrakis(mercaptomethylthio)-1,17-dimercapto-2,6,8,10,12,16-hexathiaheptadecane, 3,4,8,9-tetrakis(mercaptomethylthio)-1,11-dimercapto-2,5,7,10-tetrathiaundecane, 3,4,8,9,13,14-hexakis(mercaptomethylthio)-1,16-dimercapto-2,5,7,10,12,15-hexathiahexadecane, 8-{bis(mercaptomethylthio)methyl}-3,4,12,13-tetrakis(mercaptomethylthio)-1,15-dimercapto-2,5,7,9,11,14-hexathiapentadecane, 4,6-bis{3,5-bis(mercaptomethylthio)-7-mercapto-2,6-dithiaheptylthio}-1,3-dithiane, 4-{3,5-bis(mercaptomethylthio)-7-mercapto-2,6-dithiaheptylthio}-6-mercaptomethylthio-1,3-dithiane, 1,1-bis{4-(6-mercaptomethylthio)-1,3-dithianylthio}-3,3-bis(mercaptomethylthio)propane, 1,3-bis{4-(6-mercaptomethylthio)-1,3-dithianylthio}-1,3-bis(mercaptomethylthio)propane, 1-{4-(6-mercaptomethylthio)-1,3-dithianylthio}-3-{2,2-bis(mercaptomethylthio)ethyl}-7,9-bis(mercaptomethylthio)-2,4,6,10-tetrathiaundecane, 1-{4-(6-mercaptomethylthio)-1,3-dithianylthio}-3-{2-(1,3-dithiethanyl)}methyl-7,9-bis(mercaptomethylthio)-2,4,6,10-tetrathiaundecane, 1,5-bis{4-(6-mercaptomethylthio)-1,3-dithianylthio}-3-{2-(1,3-dithiethanyl)}methyl-2,4-dithiapentane, 4,6-bis[3-{2-(1,3-dithiethanyl)}methyl-5-mercapto-2,4-dithiapentylthio]-1,3-dithiane, 4,6-bis{4-(6-mercaptomethylthio)-1,3-dithianylthio}-1,3-dithiane, 4-{4-(6-mercaptomethylthio)-1,3-dithianylthio}-6-{4-(6-mercaptomethylthio)-1,3-dithianylthio}-1,3-dithiane, 3-{2-(1,3-dithiethanyl)}methyl-7,9-bis(mercaptomethylthio)-1,11-dimercapto-2,4,6,10-tetrathiaundecane, 9-{2-(1,3-dithiethanyl)}methyl-3,5,13,15-tetrakis(mercaptomethylthio)-1,17-dimercapto-2,6,8,10,12,16-hexathiaheptadecane, 3-{2-(1,3-dithiethanyl)}methyl-7,9,13,15-tetrakis(mercaptomethylthio)-1,17-dimercapto-2,4,6,10,12,16-hexathiaheptadecane, 3,7-bis{2-(1,3-dithiethanyl)}methyl-1,9-dimercapto-2,4,6,8-tetrathianonane, 4-{3,4,8,9-tetrakis(mercaptomethylthio)-11-mercapto-2,5,7,10-tetrathiaundecyl}-5-mercaptomethylthio-1,3-dithiolane, 4,5-bis{3,4-bis(mercaptomethylthio)-6-mercapto-2,5-dithiahexylthio}-1,3-dithiolane, 4-{3,4-bis(mercaptomethylthio)-6-mercapto-2,5-dithiahexylthio}-5-mercaptomethylthio-1,3-dithiolane, 4-{3-bis(mercaptomethylthio)methyl-5,6-bis(mercaptomethylthio)-8-mercapto-2,4,7-trithiaoctyl}-5-mercaptomethylthio-1,3-dithiolane, 2-[bis{3,4-bis(mercaptomethylthio)-6-mercapto-2,5-dithiahexylthio}methyl]-1,3-dithietane, 2-{3,4-bis(mercaptomethylthio)-6-mercapto-2,5-dithiahexylthio}mercaptomethylthiomethyl-1,3-dithietane, 2-{3,4,8,9-tetrakis(mercaptomethylthio)-11-mercapto-2,5,7,10-tetrathiaundecylthio}mercaptomethylthiomethyl-1,3-dithietane, 2-{3-bis(mercaptomethylthio)methyl-5,6-bis(mercaptomethylthio)-8-mercapto-2,4,7-trithiaoctyl}mercaptomethylthiomethyl-1,3-dithietane, 4,5-bis[1-{2-(1,3-dithiethanyl)}-3-mercapto-2-thiapropylthio]-1,3-dithiolane, 4-[1-{2-(1,3-dithiethanyl)}-3-mercapto-2-thiapropylthio]-5-{1,2-bis(mercaptomethylthio)-4-mercapto-3-thiabutylthio}-1,3-dithiolane, 2-[bis{4-(5-mercaptomethylthio-1,3-dithiolanyl)thio}]methyl-1,3-dithietane, and 4-{4-(5-mercaptomethylthio-1,3-dithiolanyl)thio}-5-[1-{2-(1,3-dithiethanyl)}-3-mercapto-2-thiapropylthio]-1,3-dithiolane, and oligomers thereof;

compounds each having an orthotrithio formic acid ester skeleton, such as tris(mercaptomethylthio)methane, tris(mercaptoethylthio)methane, 1,1,5,5-tetrakis(mercaptoethylthio)-2,4-dithiapentane, bis[4,4-bis(mercaptomethylthio)-1,3-dithiabutyl](mercaptomethylthio)methane, tris[4,4-bis(mercaptomethylthio)-1,3-dithiabutyl]methane, 2,4,6-tris(mercaptomethylthio)-1,3,5-trithiacyclohexane, 2,4-bis(mercaptomethylthio)-1,3,5-trithiacyclohexane, 1,1,3,3-tetrakis(mercaptomethylthio)-2-thiapropane, bis(mercaptomethyl)methylthio-1,3,5-trithiacyclohexane, tris

[(4-mercaptomethyl-2,5-dithiacyclohexyl-1-yl)methylthio]methane, 2,4-bis(mercaptomethylthio)-1,3-dithiacyclopentane, 2-mercaptoethylthio-4-mercaptomethyl-1,3-dithiacyclopentane, 2-(2,3-dimercaptopropylthio)-1,3-dithiacyclopentane, 4-mercaptomethyl-2-(2,3-dimercaptopropylthio)-1,3-dithiacyclopentane, 4-mercaptomethyl-2-(1,3-dimercapto-2-propylthio)-1,3-dithiacyclopentane, tris[2,2-bis(mercaptomethylthio)-1-thiaethyl]methane, tris[3,3-bis(mercaptomethylthio)-2-thiapropyl]methane, tris[4,4-bis(mercaptomethylthio)-3-thiabutyl]methane, 2,4,6-tris[3,3-bis(mercaptomethylthio)-2-thiapropyl]-1,3,5-trithiacyclohexane, and tetrakis[3,3-bis(mercaptomethylthio)-2-thiapropyl]methane, and oligomers thereof; and compounds each having an orthotetrathiocarbonic acid ester skeleton, such as 3,3'-di(mercaptomethylthio)-1,5-dimercapto-2,4-dithiapentane, 2,2'-di(mercaptomethylthio)-1,3-dithiacyclopentane, 2,7-di(mercaptomethyl)-1,4,5,9-tetrathiaspiro [4.4]nonane, and 3,9-dimercapto-1,5,7,11-tetrathiaspiro [5.5]undecane, and oligomers thereof, but are not limited to these exemplary compounds. These exemplary compounds may be used alone or in combination of two or more thereof.

Among these thiol compounds, from the viewpoint of the optical properties, in particular Abbe's numbers, of the resulting molded product, aliphatic thiol compounds are preferably selected rather than aromatic thiol compounds. Further, from the viewpoint of optical properties, in particular, requirements in refractive indices, a compound containing a sulfur atom, such as a sulfide bond and/or a disulfide bond, in addition to a thiol group is more preferably selected. From the viewpoint of heat resistance of the resulting molded product, at least one kind of compounds having three or more thiol groups are particularly preferably selected for improvement in a three-dimensional crosslinkability.

From the above-described viewpoints, examples of the preferred thiol compound include 4-mercaptomethyl-1,8-dimercapto-3,6-dithiaoctane, 4,8 or 4,7 or 5,7-dimercaptomethyl-1,11-dimercapto-3,6,9-trithiaundecane, pentaerythritol tetrakis(2-mercaptoacetate), pentaerythritol tetrakis(3-mercaptopropionate), 2,5-bis(mercaptomethyl)-1,4-dithiane, bis(mercaptoethyl)sulfide, 1,1,3,3-tetrakis(mercaptomethylthio)propane, 4,6-bis(mercaptomethylthio)-1,3-dithiane, and 2-(2,2-bis(mercaptomethylthio)ethyl)-1,3-dithietane, and can include at least one kind of polythiol compounds selected from these compounds.

As for the amount of the thiol compound contained in the polymerizable composition of the present invention, when the amount of the thiol compound to be used is too low, with respect to 100 parts by weight of the total weight of the alkyne compound represented by general formula (1) and the thiol compound, improvement in color and mechanical strength may be unfavorably reduced in some cases. Furthermore, if the amount of the thiol compound to be used is too high, with respect to 100 parts by weight of the total weight of the compound represented by general formula (1) and the thiol compound, a reduction of heat resistance may be unfavorably significant in some cases.

Therefore, the content of the thiol compound in the polymerizable composition of the present invention is preferably equal to or more than 25 parts by weight and equal to or less than 75 parts by weight with respect to 100 parts by weight of the total weight of the alkyne compound represented by general formula (1) and the thiol compound. By including the thiol compound in such a range, a molded product having a high refractive index is provided and also exhibiting excellent color, mechanical strength and heat resistance.

(Other Components)

The polymerizable composition of the present invention may further contain a known polymerization catalyst to adjust a polymerization rate, if necessary. Examples of the polymerization catalyst include peroxides such as Perbutyl O, Perhexyl O, benzoyl peroxide, and hydrogen peroxide water, and azide compounds such as azobisbutyronitrile. Use of these radical generators as a catalyst makes it possible to proceed with polymerization under mild conditions.

Depending on the intended purposes, various materials such as a resin modifier, a chain extender, a crosslinking agent, a photostabilizer represented by HALS, an ultraviolet absorber represented by a benzotriazole-based ultraviolet absorber, an antioxidant represented by a hindered phenol-based antioxidant, a coloring inhibitor, a dye or bluing agent represented by an anthraquinone-based disperse dye, a filler, an external mold releasing agent represented by a silicone-based external mold releasing agent, or an internal mold releasing agent represented by a surfactant such as acidic phosphoric ester, a quaternary ammonium salt, or a quaternary phosphonium salt, and an adhesion improving agent may be added. Herein, the internal mold releasing agent also includes those catalysts exhibiting a mold releasing effect among the various catalysts as described above.

Although the amount of each of the aforementioned various additives which can be added varies depending on the type, structure and effect of each additive and is not limited, the adding amount is usually in the range of equal to or more than 0.001% by weight and equal to or less than 10% by weight and preferably in the range of equal to or more than 0.01% by weight and equal to or less than 5% by weight, based on the total weight of the polymerizable composition. The dye is preferably used in the range of equal to or more than 1 ppb and equal to or less than 100 ppm. Within these ranges, a better cured molded product can be produced, and the resulting molded product may have better transparency and optical properties in some cases.

(Process for Producing Polymerizable Composition)

The process for producing the polymerizable composition of the present invention may be, for example, typically a method of mixing and dissolving the compound represented by general formula (1) in combination with the foregoing various other polymerizable compounds if necessary, with the addition of the foregoing polymerization catalyst if necessary.

The resulting polymerizable composition is useful as a raw material monomer composition for a transparent molded product having a very high refractive index.

The polymerizable composition of the present invention may be further purified if necessary.

Purification of the polymerizable composition is a technique which is used for improving the transparency of the molded product obtained by curing, improving the color of the molded product or increasing the purity of the molded product. As a method for purifying the polymerizable composition of the present invention, any known method, for example, recrystallization, column chromatography (for example, using silica gel, activated carbon, or an ion-exchange resin), or extraction, may be carried out with any timing as long as the transparency and color of the molded product obtained by curing the generally purified composition are improved.

The method of washing the polymerizable composition is a technique which is used for improving the transparency or color of the molded product obtained by curing. For example, there is a method in which, when the polymerizable composition is synthesized and taken out or after the polymerizable composition is synthesized and taken out, the composition is washed with a polar and/or nonpolar solvent to remove or reduce a substance deteriorating the transparency of a molded product, for example, an inorganic salt used for synthesizing the polymerizable composition or by-prepared in synthesizing the composition, such as an ammonium salt. Although the solvent to be used depends on the polymerizable composition to be cleaned and the polarity of a solution containing the polymerizable composition and is not limited, preferred is a solvent which can dissolve a component to be removed, and which is hardly compatible with the polymerizable composition to be cleaned and the solution containing the polymerizable composition. The solvent may be used singly or a mixture of two or more solvents may be used. Although the amount of a component to be removed varies depending on the purpose and application, the amount is preferably as low as possible. The amount is usually not more than 5,000 ppm and more preferably not more than 1,000 ppm, which may provide favorable results.

The thermal insulation, cold storage or filtration method for the polymerizable composition is a technique which is used for improving the transparency or hue of the molded product obtained by curing, and is generally carried out at the timing such as when the polymerizable composition is synthesized and taken out or after the polymerizable composition is synthesized and taken out. As the thermal insulation method, there is a method in which, for example, in the case where the polymerizable composition is crystallized to deteriorate handleability during storage, the polymerizable composition are dissolved by heating within a range causing no deterioration in the performance of the polymerizable composition and the molded product. Although the heating temperature range and heat dissolution method depend on the structure of the compound constituting the polymerizable composition to be handled and are not limited, the heating temperature is usually within the range of a solidification point+50° C. and preferably within the range of a solidification point+20° C. As the heat dissolution method, there is a method in which the composition is dissolved by mechanical stirring with a stirring device or bubbling with an inert gas for moving an internal liquid. The cold storage is generally carried out for improving the preservation stability of the polymerizable composition. However, for example in the case where the polymerizable composition has a high melting point, consideration may be given to the storage temperature to improve handleability after crystallization. Although the cold storage temperature depends on the structure and preservation stability of the compound constituting the polymerizable composition to be handled and is not limited, the polymerizable composition of the present invention needs to be stored at a temperature or below which can maintain the stability thereof.

Further, in the case where the polymerizable composition of the present invention is a polymerizable composition used for optical applications, such a polymerizable composition is required to have very high transparency, and thus the polymerizable composition may be usually filtered with a filter having a small pore size. Although the pore size of the filter used herein is usually equal to or greater than 0.05 μm and equal to or smaller than 10 μm, the pore size is preferably equal to or greater than 0.05 μm and equal to or smaller than 5 μm and more preferably equal to or greater than 0.1 μm and equal to or smaller than 5 μm from the viewpoints of operability and performance. The polymerizable composition of the present invention is no exception in many cases in that filtration leads to good results. Although a low filtration temperature near the solidification point produces more desirable results in some cases, there may be a case where filtration is preferably carried out at a temperature causing no trouble in the filtration work in the case where solidification proceeds during filtration.

The reduced-pressure treatment is a general means which removes a solvent, dissolved gas and odor which deteriorate the performance of the molded product prepared by curing the polymerizable composition. Since a dissolved solvent generally decreases the refractive index of the resulting molded product or deteriorates the heat resistance thereof, the dissolved solvent may be removed as much as possible. Although the permissible amount of the dissolved solvent depends on the structure of the compound constituting the polymerizable composition to be handled and the structure of the dissolved solvent and is not limited, the permissible amount is usually preferably not more than 1% and more preferably not more than 5,000 ppm. It is preferable to remove the dissolved gas from the viewpoint of suppressing the polymerization inhibition and from the viewpoint of suppressing incorporation of air bubbles into the resulting molded product. Particularly, a moisture gas such as water vapor is preferably removed by bubbling with a dry gas. The amount of the dissolved gas can be determined depending on the structure of the compound constituting the polymerizable composition, and the physical properties, structure and type of the dissolved gas.

[Molded Product]

The molded product can be obtained by polymerizing and curing the resulting polymerizable composition, usually, according to the method used when polymerizing a known thietane group-containing compound. The polymerization catalyst type and amount and the monomer type and ratio for obtaining a molded product formed of a cured resin are determined depending on the structure of the compound constituting the polymerizable composition.

Further, the molded product obtained by heat curing such a polymerizable composition can be used as an optical material.

Examples of the optical material include various plastic lenses such as a spectacle lens for vision correction, a lens for imaging equipment, a Fresnel lens for liquid crystal projectors, a lenticular lens, and a contact lens; a sealing material for a light emitting diode (LED); an optical waveguide; an optical adhesive used for the junction of an optical lens and an optical waveguide; an anti-reflection layer to be used for an optical lens or the like; and a transparent coating or transparent substrate used for a liquid crystal display member such as a substrate, a light guiding plate, a film or a sheet.

Hereinafter, the process for producing a plastic lens will be described.

Examples of the process for producing a plastic lens include various known molding methods. A typical method includes a casting polymerization.

When casting polymerization of the polymerizable composition of the present invention is carried out, the polymerizable composition is degassed under reduced pressure or filtered off using a filter if necessary, and then the polymerizable composition is poured into a molding mold and if necessary, heated for carrying out polymerization. In this case, it is preferable to carry out polymerization by slowly heating from a low temperature to a high temperature.

The aforementioned molding mold is composed of, for example, two pieces of mirror surface-ground casting molds through a gasket comprised of, for example, polyethylene, an ethylene-vinyl acetate copolymer or polyvinyl chloride. Typical examples of the casting mold include, but are not limited to, combined casting molds such as glass and glass, glass and plastic plate, and glass and metal plate. The molding mold may be two pieces of casting molds fixed by a tape such as a polyester adhesive tape. If necessary, a known process method such as mold release process may be carried out for the casting mold.

In the case of carrying out the casting polymerization, the polymerization temperature is affected by the polymerization conditions such as the type of a polymerization initiator, and is not particularly limited. The polymerization temperature is usually −50° C. to 200° C., preferably −20° C. to 170° C., and more preferably 0° C. to 150° C.

Although the polymerization time is affected by the polymerization temperature, it is usually equal to or longer than 0.01 hours and equal to or shorter than 200 hours and preferably equal to or longer than 0.05 hours and equal to or shorter than 100 hours. Polymerization can also be carried out in combination of several temperatures by conducting temperature fixation, temperature elevation, or temperature dropping, if necessary.

Furthermore, the polymerizable composition of the present invention can also be polymerized by applying an active energy ray such as an electron beam, ultraviolet light or visible light. At this time, a radical polymerization catalyst or a cationic polymerization catalyst for initiating polymerization by the active energy ray is used if necessary.

After the resulting molded product (plastic lens) is cured, it may be subjected to an annealing process if necessary. Furthermore, for purposes of anti-reflection, high hardness, wear resistance improvement, anti-fogging properties or fashionability, various known physical or chemical processes such as surface polishing, antistatic process, hard coat process, non-reflective coat process, tinting process, and photochromic process (for example, photochromic lens process) may be carried out, if necessary.

The molded product comprised of the resin obtained by polymerizing the polymerizable composition of the present invention has a high refractive index, high transparency, and good heat resistance and mechanical strength, and is useful as, for example, an optical material such as a plastic lens.

EXAMPLES

Hereinafter, the present invention will be described in more detail with reference to the following Examples, but the present invention is not limited thereto.

(Evaluation Method)

The evaluation of physical properties of molded products obtained in Examples was carried out by the following methods.

External appearance: Transparency was confirmed visually.

Refractive index: Measurement was carried out at 20° C. using a Pulfrich refractometer.

The mixture containing 1,1,3,3-tetrakis(mercaptomethylthio)propane as a main component, which is used in Examples, was produced by the method described in Japanese Laid-open Patent Publication No. 2001-342172.

Reference Production Example 1

Propargyl thioacetate (compound represented by the following formula) was synthesized.

20.0 g (0.175 mol) of potassium thioacetate (commercially available product (manufactured by Tokyo Chemical Industry Co., Ltd.)) was charged into a reactor equipped with a stirrer, and 60 g of methanol was added thereto, followed by stirring and dissolution. Subsequently, the reaction solution was cooled to 5° C. using an ice-water bath, and 20.4 g (0.172 mol) of propargyl bromide (commercially available product (manufactured by Tokyo Chemical Industry Co., Ltd.)) was charged dropwise over 1 hour, followed by continued stirring for 4 hours. The resulting salt of potassium bromide was filtered off, and the solvent was distilled off using a rotary evaporator. The resulting reaction product was dissolved in 125 g of dichloromethane, and washed twice with 30 g of water. The organic layer was separated, dried over sodium sulfate, and filtered to remove salts. The resulting residue was concentrated under reduced pressure in a rotary evaporator to give 17.80 g (yield: 80.9%, purity 89.2%) of a compound shown below (propargyl thioacetate).

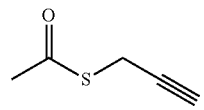

The identification data of the obtained compound are shown below.

$^1$H-NMR (solvent: CDCl$_3$, internal standard material: TMS) δ: 2.20 (1H), 2.37 (3H), 3.65 (2H).

EI-MS Found [M]$^+$: 114, Theoretical [M]$^+$: 114

Reference Production Example 2

Synthesis of Propargyl Disulfide (Compound Represented by the Following Formula (1a))

6.0 g (0.044 mol) of propargyl thioacetate synthesized in Reference Production Example 1 was charged into a reactor equipped with a stirrer, and 54 g of water was added thereto, followed by stirring and dissolution. Subsequently, the reaction solution was cooled to 10° C. using an ice-water bath, and then 10.6 g (0.132 mol) of a 50% sodium hydroxide solution (commercially available product (manufactured by Wako Pure Chemical Industries, Ltd.)) was charged to thereby synthesize propargyl thiol. Next, 40 ml (0.02 mol) of a 0.5 mol/L iodine solution (commercially available product (manufactured by Wako Pure Chemical Industries, Ltd.)) was charged dropwise over 20 minutes. This was followed by extraction with 50 g of dichloromethane and washing with 50 g of water to remove salts, followed by liquid separation. Following washing liquid separation with 50 g of a 5% sodium thiosulfate aqueous solution, liquid separation by washing with 50 g of saturated saline was carried out. The organic layer was dried over magnesium sulfate and filtered to remove salts, and then the solvent was distilled off in a rotary evaporator while being cooled in an ice-water bath. The remaining pale yellow liquid was dried under reduced pressure by a vacuum pump while being cooled in an ice-water bath, thereby affording 2.27 g (yield: 79.8%) of a compound shown below.

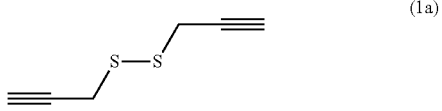

(1a)

The identification data of the obtained compound are shown below.

¹H-NMR (solvent: CDCl₃, internal standard material: TMS) δ: 2.33 (2H), 3.62 (4H).

EI-MS Found [M−H]⁺: 141, Theoretical [M]⁺: 142

Reference Production Example 3

Synthesis of Bispropargyl Thioethylene (Compound Represented by the Following Formula (1b))

6.5 g (0.069 mol) of ethanedithiol (commercially available product (manufactured by Tokyo Chemical Industry Co., Ltd.)) was charged into a reactor equipped with a stirrer, and 80 ml of methanol was added thereto, followed by stirring and dissolution. Subsequently, the reaction solution was cooled to 10° C. using an ice-water bath, and then a solution of 5.5 g (0.139 mol) of sodium hydroxide dissolved in 20 ml of water was charged thereto, followed by stirring. After cooling to 0° C., 16.5 g (0.139 mol) of propargyl bromide (commercially available product (manufactured by Tokyo Chemical Industry Co., Ltd.)) was charged dropwise, and the reaction solution was allowed to stand overnight at room temperature. The precipitated solid was collected by filtration, washed with water, and then dried under reduced pressure by a vacuum pump to give 10.0 g (yield: 85%) of a compound shown below.

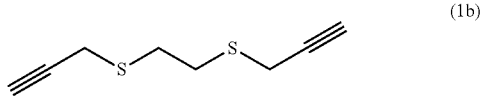

The identification data of the obtained compound are shown below.

¹H-NMR (solvent: CDCl₃, internal standard material: TMS) δ: 2.28 (2H), 2.98 (4H), 3.32 (4H).

IR (Universal ATR method) 3251, 2109, 1417, 1203, 1172, 1128, 727, 716, 681, 652, 468 cm⁻¹.

Reference Production Example 4

Synthesis of Bispropargyl Sulfide (Compound Represented by the Following Formula (1c))

3.5 g (0.021 mol) of sodium sulfide having a purity of 46.2% (commercially available product (manufactured by Sankyo Kasei Co., Ltd.)) was charged into a reactor equipped with a stirrer, and 12 ml of dimethylformamide was added thereto, followed by stirring and dissolution. Subsequently, the reaction solution was cooled to 10° C. using an ice-water bath and then 5.0 g (0.042 mol) of propargyl bromide (commercially available product (manufactured by Tokyo Chemical Industry Co., Ltd.)) was charged thereto, followed by allowing to stand overnight at room temperature. The reaction solution was discharged into 100 ml of water, extracted with 30 ml of ethyl acetate, and washed three times with 50 ml of water, followed by liquid separation. The organic layer was dried over sodium sulfate, filtered to remove salts and then dried under reduced pressure by a vacuum pump to give 1.7 g (yield: 73%) of a compound shown below.

The identification data of the obtained compound are shown below.

¹H-NMR (solvent: CDCl₃, internal standard material: TMS) δ: 2.27 (2H), 3.44 (4H).

IR (Universal ATR method) 3289, 1407, 1232, 630 cm⁻¹.

EI-MS Found [M−H]⁺: 109, Theoretical [M]⁺: 110

Reference Production Example 5

Synthesis of Bispropargyl Carbonate (Compound Represented by the Following Formula (1d))

51.8 g (0.17 mol) of triphosgene (commercially available product (manufactured by Tokyo Chemical Industry Co., Ltd.)) was charged into a reactor equipped with a stirrer, and 210 ml of methylene chloride was added thereto, followed by stirring and dissolution. Subsequently, the reaction solution was cooled to 10° C. using an ice-water bath, and then a solution of 60.0 g (1.07 mol) of propargyl alcohol (commercially available product (manufactured by Tokyo Chemical Industry Co., Ltd.)) and 84.5 g (1.07 mol) of pyridine (commercially available product (manufactured by Wako Pure Chemical Industries, Ltd.)) dissolved in 210 ml of methylene chloride was charged dropwise thereto over 1.5 hours, followed by stirring for another 3 hours. Subsequently, a solution of 10.4 g (0.035 mol) of triphosgene and 16.9 g (0.21 mol) of pyridine dissolved in 210 ml of methylene chloride was charged thereto, followed by stirring for another 2 hours. This was followed by liquid separation washing with water, a 5% HCl aqueous solution, water, a 5% NaHCO₃ aqueous solution, and water. The organic layer was dried over magnesium sulfate and filtered to remove salts, and then the solvent was distilled off in a rotary evaporator. The resulting residue was dried under reduced pressure by a vacuum pump to give 59.2 g (yield: 80.3%) of a compound shown below.

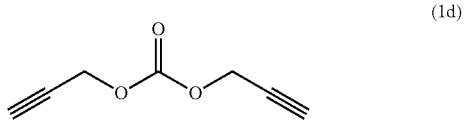

The identification data of the obtained compound are shown below.

¹H-NMR (solvent: CDCl₃, internal standard material: TMS) δ: 2.55 (2H), 4.76 (4H).

IR (Universal ATR method) 3293, 2131, 1749, 1439, 1232, 979, 916, 785, 638, 524 cm⁻¹.

Example 1

Synthesis of Bispropargyl Thiomethylene (Compound Represented by the Following Formula (1e))

37.8 g (0.25 mol) of propargyl bromide (commercially available product (manufactured by Tokyo Chemical Industry Co., Ltd.)) was charged into a reactor equipped with a stirrer, and 115 ml of toluene was added thereto, followed by stirring and dissolution. Subsequently, the reaction solution was cooled to 10° C. using an ice-water bath and then 10.0 g (0.125 mol) of methanedithiol and 25.3 g (0.25 mol) of triethylamine (commercially available product (manufactured by Wako Pure Chemical Industries, Ltd.)) were charged thereto, followed by stirring at room temperature. Water was charged to carry out liquid separation washing. The organic layer was dried over magnesium sulfate and filtered to remove salts, and then the solvent was distilled off in a rotary evaporator. The remaining liquid was purified by column chromatography to give 13.56 g (yield: 69.5%) of a compound shown below.

(1e)

The identification data of the obtained compound are shown below.
$^1$H-NMR (solvent: CDCl$_3$, internal standard material: TMS) δ: 2.26 (2H), 3.38 (4H), 4.02 (2H).

Example 2

Synthesis of Bispropargyl Thiocarbonate (Compound Represented by the Following Formula (1f))

9.9 g (0.033 mol) of triphosgene (commercially available product (manufactured by Tokyo Chemical Industry Co., Ltd.)) was charged into a reactor equipped with a stirrer, and 70 ml of methylene chloride was added thereto, followed by stirring and dissolution. Subsequently, the reaction solution was cooled to 10° C. using an ice-water bath and then a solution of 11.0 g (0.017 mol) of propargyl thiol (produced by the method of Reference Production Example 2) and 13.2 g (0.017 mol) of pyridine dissolved in 70 ml of methylene chloride was charged dropwise over 1 hour, followed by further stirring for 1.5 hours and then stirring at room temperature for 1.5 hours. The reaction was stopped with a saturated aqueous NaHCO$_3$ solution, followed by liquid separation washing with water, a 5% HCl aqueous solution, water, a 5% NaHCO$_3$ aqueous solution, and water. The organic layer was dried over magnesium sulfate. This was followed by filtration to remove salts and the solvent was distilled off in a rotary evaporator. The resulting residue was dried under reduced pressure by a vacuum pump to give 3.8 g (yield: 53.4%) of a compound shown below.

(1f)

The identification data of the obtained compound are shown below.
$^1$H-NMR (solvent: CDCl$_3$, internal standard material: TMS) δ: 2.35 (2H), 3.79 (4H).

Example 3

Synthesis of Bispropargyl Thiocarbamate (Compound Represented by the Following Formula (1g))

24.3 g (0.05 mol) of a toluene solution of 2.06 mmol/g of propargyl thiol (produced by the method of Reference Production Example 2) was charged into a screw tube to which 10 ml of toluene was then added, followed by stirring. Subsequently, 4.1 g (0.05 mol) of propargyl isocyanate was charged thereto, followed by stirring at room temperature for 2 days. Silica gel was charged thereto, followed by stirring, and silica gel was filtered off. The solvent was distilled off in a rotary evaporator and then the resulting residue was dried under reduced pressure by a vacuum pump to give 5.72 g (yield: 74.7%) of a compound shown below.

(1g)

The identification data of the obtained compound are shown below.
$^1$H-NMR (solvent: CDCl$_3$, internal standard material: TMS) δ: 2.23 (1H), 2.28 (1H), 3.71 (2H), 4.12 (2H), 5.54 (1H).

Example 4

Synthesis of 2,4-bis(propargylthio)-2,5-dihydro-1,2-thiastibole (Compound Represented by the Following Formula (1h))

14.8 g (0.10 mol) of propargyl thioacetate synthesized in Reference Production Example 1 was charged into a reactor equipped with a stirrer, and 100 g of methanol was added thereto, followed by stirring and dissolution. Subsequently, the reaction solution was cooled to 10° C. using an ice-water bath and then 12.9 g (0.067 mol) of a 28% sodium methoxide methanol solution was charged dropwise over 1 hour. Next, a solution of 5.0 g (0.022 mol) of antimony chloride (commercially available product (manufactured by Wako Pure Chemical Industries, Ltd.)) dissolved in 20 g of ethanol was charged dropwise over 20 minutes. This was followed by stirring for 15 hours, and the precipitated solid was collected by filtration. The precipitate was dissolved in 50 g of dichloromethane and washed with 50 g of water to remove salts, followed by liquid separation. The organic layer was dried over magnesium sulfate and filtered to remove salts, and then the solvent was distilled off in a rotary evaporator. The remaining yellow solid was dried to give 4.60 g (yield: 62.4%) of a compound shown below.

(1h)

The identification data of the obtained compound of Formula (1h) are shown below.
$^1$H-NMR (solvent: DMSO-d6, internal standard material: TMS) δ: 3.18 (2H), 3.43 (2H), 3.78 (2H), 4.09 (1H), 4.45 (1H), 6.74 (1H).
$^{13}$C-NMR (solvent: DMSO-d6) δ: 16.0, 20.7, 43.9, 73.5, 73.9, 79.6, 83.6, 126.9, 156.1
IR (Universal ATR method): 3281, 1553, 1407, 1238, 1183, 9652, 629 cm$^{-1}$.
FAB-MS Found [M+H]$^+$: 335, Theoretical [M]$^+$: 334

Example 5

0.43 g of the compound produced in Reference Production Example 2 was weighed in a glass beaker at room temperature (25° C.), followed by weighing 0.57 g of a mixture containing 1,1,3,3-tetrakis(mercaptomethylthio) propane as a main component. Stirring and mixing were carried out while cooling to 10° C., so that degassing under reduced pressure was carried out. The glass beaker was placed in the reactor and then allowed to stand for 7 days while cooling to 10° C. Then, the reaction system was heated to 80° C. over 1 hour using an oil bath. The reaction system was transferred to a polymerization oven, followed by heating polymerization at 110° C. for 3 hours.

The resulting resin molded product had a transparent appearance and a refractive index ne of 1.745.

Example 6

0.27 g of the compound produced in Reference Production Example 2 was weighed in a glass beaker at room temperature (25° C.), followed by weighing a mixture containing 0.73 g of 1,1,3,3-tetrakis(mercaptomethylthio) propane as a main component. Stirring and mixing were carried out while cooling to 10° C., so that degassing under reduced pressure was carried out. The glass beaker was placed in the reactor and then allowed to stand for 7 days while cooling to 10° C. Then, the reaction system was heated to 80° C. over 1 hour using an oil bath. The reaction system was transferred to a polymerization oven, followed by heating polymerization at 100° C. for 2 hours.

The resulting resin molded product had a transparent appearance and a refractive index ne of 1.732.

Example 7

0.50 g of the compound produced in Reference Production Example 2 was weighed in a glass beaker at room temperature (25° C.), followed by weighing 0.50 g of a mixture containing 1,1,3,3-tetrakis(mercaptomethylthio) propane as a main component. Stirring and mixing were carried out while cooling to 10° C., so that degassing under reduced pressure was carried out. The glass beaker was placed in the reactor and allowed to stand for 3 hours while cooling to 10° C. and then allowed to stand for 2 days at room temperature (25° C.). The reaction system was warmed to 60° C. over 8 hours and then transferred to a polymerization oven where the temperature was raised from 60° C. to 100° C. over 9 hours, followed by heating polymerization at 100° C. for 3 hours.

The resulting resin molded product had a transparent appearance and a refractive index ne of 1.732.

Example 8

0.47 g of the compound produced in Reference Production Example 2 was weighed in a glass beaker at room temperature (25° C.), followed by weighing 0.53 g of 4-mercaptomethyl-1,8-dimercapto-3,6-dithiaoctane. Stirring and mixing were carried out while cooling to 10° C., so that degassing under reduced pressure was carried out. The glass beaker was placed in the reactor and allowed to stand for 3 hours while cooling to 10° C. and then allowed to stand for 2 days at room temperature (25° C.). The reaction system was warmed to 60° C. over 8 hours and then transferred to a polymerization oven where the temperature was raised from 60° C. to 100° C. over 9 hours, followed by heating polymerization at 100° C. for 3 hours.

The resulting resin molded product had a transparent appearance and a refractive index ne of 1.692.

Example 9

0.25 g of the compound produced in Reference Production Example 2 was weighed in a glass beaker at room temperature (25° C.), followed by weighing 0.75 g of a mixture containing 4-mercaptomethyl-1,8-dimercapto-3,6-dithiaoctane as a main component. Stirring and mixing were carried out, so that degassing under reduced pressure was carried out. The reaction system was transferred to a polymerization oven where the temperature was raised from 25° C. to 120° C. over 22 hours, followed by heating polymerization.

The resulting resin molded product had a transparent appearance and a refractive index ne of 1.730.

Example 10

0.25 g of the compound produced in Reference Production Example 5 was weighed in a glass beaker at room temperature (25° C.), followed by weighing 0.75 g of a mixture containing 1,1,3,3-tetrakis(mercaptomethylthio) propane as a main component. Stirring and mixing were carried out while cooling to 10° C., so that degassing under reduced pressure was carried out. The reaction system was transferred to a polymerization oven where the temperature was raised from 25° C. to 100° C. over 22 hours, followed by heating polymerization. The resulting resin molded product had a transparent appearance and a refractive index ne of 1.697.

Example 11

0.27 g of the compound produced in Reference Production Example 5 was weighed in a glass beaker at room temperature (25° C.), followed by weighing 0.73 g of a mixture containing 4,8 or 4,7 or 5,7-dimercaptomethyl-1,11-dimercapto-3,6,9-trithiaundecane as a main component. Stirring and mixing were carried out while cooling to 10° C., so that degassing under reduced pressure was carried out. The reaction system was transferred to a polymerization oven where the temperature was raised from 25° C. to 100° C. over 22 hours, followed by heating polymerization. The resulting resin molded product had a transparent appearance and a refractive index ne of 1.668.

Example 12

0.27 g of the compound produced in Example 1 was weighed in a glass beaker at room temperature (25° C.), followed by weighing 0.73 g of a mixture containing 1,1,3,3-tetrakis(mercaptomethylthio)propane as a main component. Stirring and mixing were carried out while cooling to 10° C., so that degassing under reduced pressure was carried out. The reaction system was transferred to a polymerization oven where the temperature was raised from 25° C. to 100° C. over 22 hours, followed by heating polymerization. The resulting resin molded product had a refractive index ne of 1.743.

Example 13

0.30 g of the compound produced in Example 1 was weighed in a glass beaker at room temperature (25° C.), followed by weighing 0.70 g of a mixture containing 4,8 or 4,7 or 5,7-dimercaptomethyl-1,11-dimercapto-3,6,9-trithiaundecane as a main component. Stirring and mixing were carried out while cooling to 10° C., so that degassing under reduced pressure was carried out. The reaction system was transferred to a polymerization oven where the temperature was raised from 25° C. to 100° C. over 22 hours, followed by heating polymerization. The resulting resin molded product had a refractive index ne of 1.696.

Example 14

0.29 g of the compound produced in Example 2 was weighed in a glass beaker at room temperature (25° C.), followed by weighing 0.71 g of a mixture containing 1,1,3,3-tetrakis(mercaptomethylthio)propane as a main component. Stirring and mixing were carried out while cooling to 10° C., so that degassing under reduced pressure was carried out. The reaction system was transferred to a polymerization oven where the temperature was raised from 25° C. to 100° C. over 22 hours, followed by heating polymerization. The resulting resin molded product had a transparent appearance and a refractive index ne of 1.741.

Example 15

0.32 g of the compound produced in Example 2 was weighed in a glass beaker at room temperature (25° C.), followed by weighing 0.68 g of a mixture containing 4,8 or 4,7 or 5,7-dimercaptomethyl-1,11-dimercapto-3,6,9-trithiaundecane as a main component. Stirring and mixing were carried out while cooling to 10° C., so that degassing under reduced pressure was carried out. The reaction system was transferred to a polymerization oven where the temperature was raised from 25° C. to 100° C. over 22 hours, followed by heating polymerization. The resulting resin molded product had a transparent appearance and a refractive index ne of 1.709.

Example 16

0.27 g of the compound produced in Example 3 was weighed in a glass beaker at room temperature (25° C.), followed by weighing 0.73 g of a mixture containing 1,1,3,3-tetrakis(mercaptomethylthio)propane as a main component. Stirring and mixing were carried out while cooling to 10° C., so that degassing under reduced pressure was carried out. The reaction system was transferred to a polymerization oven where the temperature was raised from 25° C. to 100° C. over 22 hours, followed by heating polymerization. The resulting resin molded product had a transparent appearance and a refractive index ne of 1.730.

Example 17

0.30 g of the compound produced in Example 3 was weighed in a glass beaker at room temperature (25° C.), followed by weighing 0.70 g of a mixture containing 4,8 or 4,7 or 5,7-dimercaptomethyl-1,11-dimercapto-3,6,9-trithiaundecane as a main component. Stirring and mixing were carried out while cooling to 10° C., so that degassing under reduced pressure was carried out. The reaction system was transferred to a polymerization oven where the temperature was raised from 25° C. to 120° C. over 22 hours, followed by heating polymerization. The resulting resin molded product had a transparent appearance and a refractive index ne of 1.698.

Example 18

0.67 g of the compound of Formula (1h) produced in Example 4 was weighed in a glass beaker at room temperature (25° C.), followed by weighing 0.52 g of 4-mercaptomethyl-1,8-dimercapto-3,6-dithiaoctane. The reaction mixture was dissolved by heating to 80° C. After cooling to 70° C., 1 mg (0.1 parts by weight) of t-butyl 2-perethylhexanoate (commercially available product (manufactured by Nippon Oil & Fats Co., Ltd.)) as a polymerization catalyst was added thereto, followed by degassing under reduced pressure, and the polymerizable compound was injected into a casting mold comprised of glass mold and a tape. The casting mold was placed in a heating oven, such that polymerization was carried out at 90° C. for 16 hours and at 100° C. for 3 hours.

The resulting resin molded product had a transparent appearance and a refractive index ne of 1.795.

Resin molded products were produced in the same manner as in Example 5, except that the compound produced in Reference Production Example 3 or 4 was used. All of the resulting resin molded products had a transparent appearance and a refractive index ne of about 1.7 to 1.8.

This application claims the benefit of priority to Japanese Patent Application No. 2015-024228 filed on Feb. 10, 2015 and Japanese Patent Application No. 2015-024229 filed on Feb. 10, 2015, the disclosures of which are incorporated by reference herein in their entirety.

The present invention also includes the following aspects.

[a1] A novel sulfur-containing alkyne compound represented by the following general formula (1-6).

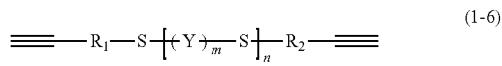

wherein, in the formula, $R_1$ and $R_2$ represent an alkylene chain having 1 or 2 carbon atoms and may be the same or different from each other, Y represents an alkylene chain having 1 or 2 carbon atoms, and m and n each represent an integer of 0 or more.

[a2] A polymerizable composition including the sulfur-containing alkyne compound according to [a1].

[a3] The polymerizable composition according to [a2], further including a thiol compound.

[a4] The polymerizable composition according to [a3], in which the thiol compound includes at least one kind of polythiol compounds selected from 4-mercaptomethyl-1,8-dimercapto-3,6-dithiaoctane, 4,8 or 4,7 or 5,7-dimercaptomethyl-1,11-dimercapto-3,6,9-trithiaundecane, pentaerythritol tetrakis(2-mercaptoacetate), pentaerythritol tetrakis(3-mercaptopropionate), 2,5-bis(mercaptomethyl)-1,4-dithiane, bis(mercaptoethyl)sulfide, 1,1,3,3-tetrakis(mercaptomethylthio)propane, 4,6-bis(mercaptomethylthio)-1,3-dithiane, and 2-(2,2-bis(mercaptomethylthio)ethyl)-1,3-dithietane.

[a5] A molded product obtained by curing the polymerizable composition according to any one of [a2] to [a4].

[a6] An optical material comprised of the molded product according to [a5].

[a7] A plastic lens comprised of the molded product according to [a5].

The present invention also further includes the following aspects.

[b1] A novel antimony-containing compound represented by the following Formula (1h).

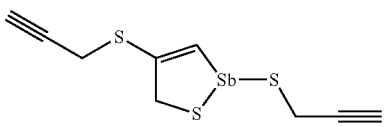
(1h)

[b2] A polymerizable composition including the antimony-containing compound according to [b1].

[b3] The polymerizable composition according to [b2], further including a thiol compound.

[b4] The polymerizable composition according to [b3], in which the thiol compound includes at least one kind of polythiol compounds selected from 4-mercaptomethyl-1,8-dimercapto-3,6-dithiaoctane, 4,8 or 4,7 or 5,7-dimercaptomethyl-1,11-dimercapto-3,6,9-trithiaundecane, pentaerythritol tetrakis mercaptoacetate, pentaerythritol tetrakis mercaptopropionate, 2,5-bis(mercaptomethyl)-1,4-dithiane, bis(mercaptoethyl)sulfide, 1,1,3,3-tetrakis(mercaptomethylthio)propane, 4,6-bis(mercaptomethylthio)-1,3-dithiane, and 2-(2,2-bis(mercaptomethylthio)ethyl)-1,3-dithietane.

[b5] A molded product obtained by curing the polymerizable composition according to any one of [b2] to [b4].

[b6] An optical material comprised of the molded product according to [b5].

[b7] A plastic lens comprised of the molded product according to [b5].

[b8] A process for producing an antimony-containing compound represented by the following Formula (1h), including reacting a thioacetylation product of propargyl or a propargyl thiol with an antimony halide in the presence of a reaction-inert solvent and a base.

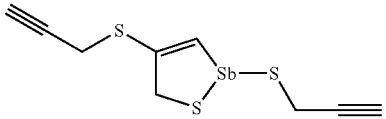
(1h)

The invention claimed is:

1. A polymerizable composition comprising an alkyne compound represented by the following general formula (1):

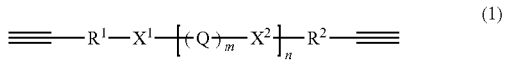
(1)

wherein, in general formula (1), $X^1$ and $X^2$ represent a sulfur atom, an oxygen atom, or an NH group and may be the same or different from each other, Q represents an alkylene group having 1 or 2 carbon atoms, a carbonyl group, or a thiophenylene group in which one of carbon atoms is substituted by an antimony atom, $R^1$ and $R^2$ represent an alkylene group having 1 or 2 carbon atoms and may be the same or different from each other, and m and n each represent 0 or 1, and further comprising a thiol compound.

2. The polymerizable composition according to claim 1, comprising an alkyne compound represented by the following general formula (2) or (3):

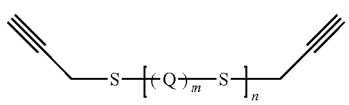
(2)

wherein, in general formula (2), Q represents an alkylene group having 1 or 2 carbon atoms, or a thiophenylene group in which one of carbon atoms is substituted by an antimony atom, and m and n each represent 0 or 1,

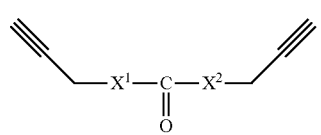
(3)

wherein, in general formula (3), $X^1$ and $X^2$ represent a sulfur atom, an oxygen atom, or an NH group and may be the same or different from each other.

3. The polymerizable composition according to claim 1, wherein the thiophenylene group in which one of carbon atoms is substituted by an antimony atom is a divalent group represented by the following Formula (4):

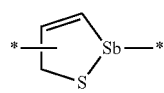
(4)

wherein, in general formula (4), * represents a bonding hand.

4. The polymerizable composition according to claim 1, wherein the thiol compound includes at least one kind of polythiol compounds selected from 4-mercaptomethyl-1,8-dimercapto-3,6-dithiaoctane, 4,8 or 4,7 or 5,7-dimercaptomethyl-1,11-dimercapto-3,6,9-trithiaundecane, pentaerythritol tetrakis(2-mercaptoacetate), pentaerythritol tetrakis(3-mercaptopropionate), 2,5-bis(mercaptomethyl)-1,4-dithiane, bis(mercaptoethyl)sulfide, 1,1,3,3-tetrakis (mercaptomethylthio)propane, 4,6-bis (mercaptomethylthio)-1,3-dithiane, and 2-(2,2-bis (mercaptomethylthio)ethyl)-1,3-dithietane.

5. A molded product obtained by curing the polymerizable composition according to claim 1.

6. An optical material comprised of the molded product according to claim 5.

7. A plastic lens comprised of the molded product according to claim 5.

* * * * *